US008858076B2

(12) United States Patent
Quintana et al.

(10) Patent No.: US 8,858,076 B2
(45) Date of Patent: Oct. 14, 2014

(54) MULTI-STEP CONTRAST SENSITIVITY GAUGE

(75) Inventors: Enrico C. Quintana, Albuquerque, NM (US); Kyle R. Thompson, Albuquerque, NM (US); David G. Moore, Albuquerque, NM (US); Jack D. Heister, Albuquerque, NM (US); Richard W. Poland, Aiken, SC (US); John P. Ellegood, Aurora, CO (US); George K. Hodges, Arab, AL (US); James E. Prindville, Lincoln, CA (US)

(73) Assignee: Sandia Corporation, Albuquerque, NM (US)

( * ) Notice: Subject to any disclaimer, the term of this patent is extended or adjusted under 35 U.S.C. 154(b) by 451 days.

(21) Appl. No.: 13/241,569

(22) Filed: Sep. 23, 2011

(65) Prior Publication Data

US 2013/0022176 A1 Jan. 24, 2013

Related U.S. Application Data

(60) Provisional application No. 61/509,493, filed on Jul. 19, 2011.

(51) Int. Cl.
*A61B 6/03* (2006.01)
*G21K 1/10* (2006.01)

(52) U.S. Cl.
CPC .................................... *G21K 1/10* (2013.01)
USPC .................................... 378/207; 378/18

(58) Field of Classification Search
USPC .................................... 378/18, 79, 205, 207
See application file for complete search history.

(56) References Cited

U.S. PATENT DOCUMENTS

| | | | | |
|---|---|---|---|---|
| 5,095,499 | A * | 3/1992 | Wentz | 378/37 |
| 5,619,548 | A | 4/1997 | Koppel | |
| 6,408,054 | B1 | 6/2002 | Rahn et al. | |
| 6,912,266 | B2 | 6/2005 | Spahn | |
| 7,471,767 | B2 | 12/2008 | Spahn | |
| 2007/0183584 | A1 | 8/2007 | Baumann et al. | |
| 2011/0063571 | A1 | 3/2011 | Duffy | |

OTHER PUBLICATIONS

"Standard Practice for Determining Contrast Sensitivity in Radiology", ASTM International Standard E1647. Retrieved at <<http://www.astm.org/Standards/E1647.htm>>, Retrieval Date: Jul. 19, 2011. pp. 1-5.

* cited by examiner

*Primary Examiner* — Hoon Song
(74) *Attorney, Agent, or Firm* — Medley Behrens & Lewis LLC; Gregory M. Doudnikoff

(57) ABSTRACT

An X-ray contrast sensitivity gauge is described herein. The contrast sensitivity gauge comprises a plurality of steps of varying thicknesses. Each step in the gauge includes a plurality of recesses of differing depths, wherein the depths are a function of the thickness of their respective step. An X-ray image of the gauge is analyzed to determine a contrast-to-noise ratio of a detector employed to generate the image.

20 Claims, 6 Drawing Sheets

MULTI-STEP CONTRAST SENSITIVITY GAUGE

This application claims the priority under 35 U.S.C. §119 (e)(1) of provisional application Ser. No. 61/509,493 filed Jul. 19, 2011 and incorporated herein by reference.

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

X-ray imaging has been in use for well over a century. X-ray imaging works generally as follows: an X-ray system includes a source of radiation that is configured to project a heterogeneous beam of X-rays onto a target. According to the density and composition of the different areas of the target, a proportion of X-rays are absorbed by the target. The X-ray system also includes a detector that is configured to detect X-rays that pass through the target. An amount of attenuation in the X-rays caused by portions of the target is indicative of a superimposition of structures of the target.

Generally, when utilization of X-ray systems is discussed, it is in reference to medical imaging. In many cases, however, X-ray technologies can be employed in non-medical settings (e.g., industrial settings). For instance, X-ray imaging may be desirably employed to ascertain density of a structural support and/or locate abnormalities in the structural support. This can allow for an inspector of the structural support to perform a failure analysis with respect to such support.

In another exemplary embodiment, X-ray imaging may be desirably employed in industrial settings for analysis of sealed motor blocks, thereby allowing an inspector to visually ascertain a flaw in a motor block when disassembly of the motor block would otherwise be required to locate the flaw. In still yet another example, X-ray imaging can be employed in connection with analyzing casings and internal components of large-scale weaponry. It can, therefore, be ascertained that there are numerous applications outside of medical imaging where X-ray imaging may desirably be employed.

When ascertaining the quality of an X-ray image, three elements are generally considered: contrast, spatial resolution, and noise. For X-ray images generated through utilization of relatively low energies (below 1 million electron volts (MeV)), there are methods to quantify contrast in X-ray images that are based upon the utilization of a predefined gauge. Such gauge, however, is ill-suited for characterizing any of the aforementioned elements when energies larger than 1 MeV are employed to drive a radiation source.

SUMMARY

The following is a brief summary of subject matter that is described in greater detail herein. This summary is not intended to be limiting as to the scope of the claims.

Described herein are various technologies pertaining to characterizing contrast to noise ratio corresponding to a detector in an X-ray system through utilization of a multi-step contrast sensitivity gauge. This characterization can be quantitative in nature, such that a reviewer of an image generated by way of the X-ray system can, with some certainty, determine that for a given thickness of a target, a feature with a thickness of some percentage of the thickness of the target (e.g., 1%, 2%, or 4%) can be distinguished in the image. Based at least in part upon such characterization of the contrast-to-noise ratio of the detector, at least one operating condition of the X-ray system can be adjusted. For instance, exposure time may be increased to improve the contrast-to-noise ratio. In another example, a number of images averaged to create a final image can be increased or decreased.

The multi-step contrast sensitivity gauge includes a plurality of steps, where each step in the plurality of the steps has a different thickness. In an example, the multi-step contrast sensitivity gauge may be a unitary structure. In another exemplary embodiment, the multi-step contrast sensitivity gauge can be composed of a plurality of modular steps that can be coupled to one another by way of one or more fasteners. For instance, each of these steps may have a threaded aperture therein that is configured to receive a threaded fastener. A bracket can include apertures that correspond to the apertures in the modular steps, and the bracket, together with the threaded fasteners, can be employed to couple the modular steps to generate a multi-step contrast sensitivity gauge.

Each step in the multi-step gauge may have a top planar surface and a bottom planar surface, wherein the thickness of a particular step is the distance between the top planar surface and the bottom planar surface. If the multi-step contrast sensitivity gauge is a unitary structure, then the bottom surface can be shared for a plurality of different steps. If the multi-step gauge is composed of a plurality of modular steps, then each modular step will have its own bottom planar surface. When coupled together, bottom planar surfaces of different steps can be coplanar.

For each step in the multi-step contrast sensitivity gauge, the top planar surface can comprise a plurality of recesses of differing depths. That is, for example, a first recess in the top planar surface may be of a first depth, a second recess in the top planar surface may be of a second depth, and a third recess in the top planar surface may be of a third depth. For instance, the depths can be a function of the thickness of the respective step to which the recesses belong. In an example, the first recess may have a depth that is 1% of the thickness of the step, the second recess may have a depth that is 2% of the thickness of the step, and the third recess may have a depth that is 4% of the thickness of the step.

In operation, the multi-step contrast sensitivity gauge is positioned relative to a source in an X-ray machine, such that X-rays emitted from the source are projected onto the target, initially incident upon the recesses in the steps of the multi-step contrast sensitivity gauge. As the X-rays pass through the multi-step gauge, at least some of the X-rays will be at least partially attenuated, and such attenuation can be detected by the detector. The resultant image can be analyzed to ascertain a contrast-to-noise ratio for the multi-step contrast sensitivity gauge at desired thicknesses and recess depths.

Other aspects will be appreciated upon reading and understanding the attached figures and description.

DETAILED DESCRIPTION

Figure 1:
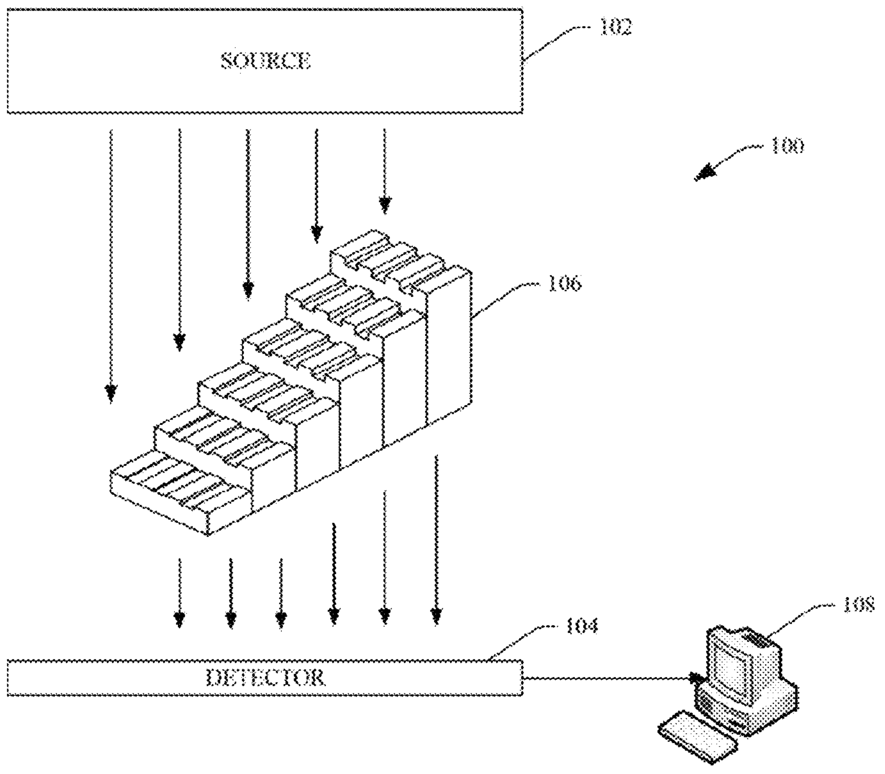
FIG. 1 is a functional block diagram of an exemplary system that facilitates characterizing contrast-to-noise ratio of a detector in an X-ray system.

Various technologies pertaining to a multi-step contrast sensitivity gauge that is utilized to characterize contrast-to-noise ratio of a detector in an X-ray system that emits X-rays at energies above 1 MeV will now be described with reference to the drawings, where like reference numerals represent like elements throughout. Additionally, as used herein, the term "exemplary" is intended to mean serving as an illustration or example of something, and is not intended to indicate a preference.

Referring now to FIG. 1, an exemplary system 100 that facilitates characterizing contrast-to-noise ratio of a detector of an X-ray system is illustrated. The system 100 comprises a source 102 that is configured to heterogeneously output X-ray beams at energies of 1 MeV and above. The system 100 further comprises a detector 104 that can be any suitable type of detector. For example, the detector 104 can comprise a phosphor plate that is subjected to X-ray beams. After the plate is X-rayed, excited electrons in the phosphor are retained in the lattice of the plate until stimulated by a laser beam passed over a surface of the plate, thereby causing light to be emitted from the plate. This light is captured and converted to an image through computer-implemented imaging technologies. In another exemplary embodiment, the detector 104 can comprise an amorphous silicon X-ray panel that includes a scintillating screen thereon that converts X-ray energy into light that is sensed by an array of transistors. Such light can be converted into an electrical signal, which is then utilized to generate the image. Other types of detector systems are also contemplated and are intended to fall under the scope of the hereto-appended claims.

The system 100 further comprises a multi-step contrast sensitivity gauge 106 that can be employed in connection with characterizing a contrast-to-noise ratio/contrast sensitivity of the detector 104. The multi-step contrast sensitivity gauge 106 comprises a plurality of steps of varying thicknesses, wherein each step in the plurality of steps includes a top planar surface and a plurality of recesses, and where depths of the recesses for a particular step are a function of a thickness of the step. Additional detail pertaining to the structure of the multi-step contrast sensitivity gauge 106 will be provided below. The multi-step contrast sensitivity gauge 106 can be composed of any suitable material. For instance, the gauge 106 can be composed of stainless steel, aluminum, brass, Poly(methyl methacrylate), a composite, or any other suitable material. The material of the gauge 106 is selected based upon composition of a target that is desirably imaged. For instance, if a stainless steel motor casing is desirably imaged, then the gauge 106 can be composed of stainless steel.

Pursuant to an example, the detector 104 can be configured to produce analog X-ray images, and the contrast-to-noise ratio can be computed based upon a visual analysis by a reviewer of the resulting image. In X-ray imaging, contrast is the difference in gray levels between objects that are in close proximity in an image. Radiography provides a measure of the attenuation of an X-ray beam as it passes through a target. Accordingly, the contrast depends on the variation of materials within the target being inspected, as well as the ability of the detector 104 to measure incident photons after they have passed through the component being inspected. An exemplary metric for defining contrast in an image is contrast-to-noise ratio, which can be defined as follows:

$$CNR = \frac{|A - B|}{\sigma}$$

where CNR is the contrast-to-noise ratio, A is the average intensity around an inspected feature (a recess in the gauge 106) in an image, B is the average intensity of the feature (the recess) in the image, and $\sigma$ is the noise in A.

As mentioned above, the detector 104 can be configured to output an analog image, wherein the contrast-to-noise ratio can be estimated based upon a visual inspection of the resultant image. In another exemplary embodiment, the detector 104 can be used in connection with generating a digital image that is processable by a computing system 108 (e.g., comprising pixels with known intensity values, where a pixel is an elementary unit of an image). That is, the computing system 108 can be configured with software that can undertake digital image analysis. The software can have knowledge of the position of the multi-step contrast sensitivity gauge 106 relative to the source 102 and the detector 104, such that the software is able to automatically ascertain locations in the image where the recesses of the steps in the multi-step gauge 106 are to appear. Alternatively, the location of the recesses in the multi-step gauge 106 in the image can be manually specified by a user.

Intensities of first pixels in the image that correspond to a particular recess in a step of the multi-step gauge 106 can be compared with intensities of second pixels in the image that are adjacent to the first pixels. This can be undertaken for numerous steps with differing thicknesses and multiple recesses of varying depths.

The system 100 may be particularly advantageously employed in inspection systems that are outside of the medical imaging field where it is desirable to measure contrast-to-noise ratio over a range of thicknesses and for multiple materials. For example, the system 100 can be employed when the X-ray system is desirably utilized to generate images of relatively thick materials for alterations in density and/or faults that may exist in such materials. Further, the system 100 can be employed when it is desirable to obtain images of systems that are enclosed with a relatively thick enclosure (such as a motor casing, weapons casing, etc.). Accordingly, the source 102 can generate photons using energy levels that are greater than 1 MeV. In an example, the source 102 can cause photons to be generated at energy levels greater than 5 MeV, greater than 10 MeV, greater than 15 MeV, or greater than 20 MeV. Heretofore there has been no suitable technique for characterizing contrast-to-noise ratio for detectors when energy levels utilized to generate an image are above 1 MeV, and where it is desirably to characterize contrast-to-noise ratio over ranges of thicknesses.

Based at least in part upon the contrast-to-noise ratio generated by the computing system 108, at least one operating condition of the detector 104 can be altered. In an example, an operator of an X-ray system may wish to be able to detect a feature in a particular entity that is approximately five inches thick and the feature is approximately 1% of the thickness of the entity (0.05 inches). The multi-step contrast sensitivity gauge 106 can be composed of the same material as the particular entity, and can include a step with a thickness of 5 inches and a recess that has a depth of 1% of such thickness (0.05 inches). The contrast-to-noise ratio, with respect to that recess in the image, can be computed, and an operating condition of the detector 104 can be altered based at least in part upon the computed contrast-to-noise ratio. For instance, if the contrast-to-noise ratio is insufficient (e.g., below a threshold), then an exposure time of the detector 104 can be increased. In another exemplary embodiment, to enhance the contrast-to-noise ratio, a number of images averaged to output a final digital image in radiography can be increased. In still yet another exemplary embodiment, an amount of energy employed by the source 102 to generate X-ray beams can be increased to improve the contrast-to-noise ratio.

Figure 2:
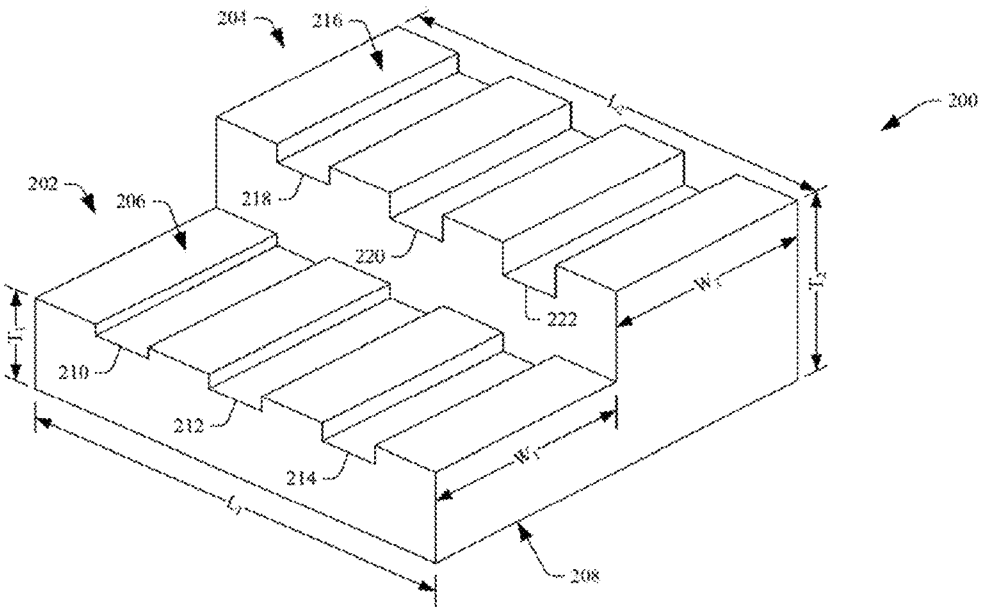
FIG. 2 is a perspective view of an exemplary multi-step contrast sensitivity gauge that can be employed in connection with characterizing contrast-to-noise ratio of a detector in an X-ray system.

With reference now to FIG. 2, an exemplary multi-step contrast sensitivity gauge 200 is illustrated. The gauge 200 comprises a first step 202 and a second step 204. While the gauge 200 is shown as including two steps, it is to be understood that a contrast sensitivity gauge may include numerous steps (e.g. six steps, eight steps, ten steps). The first step 202 comprises a first planar top face 206 and a first planar bottom face 208. The first planar top face 206 is parallel to the first planar bottom face 208. The first step 202 has a first thickness $T_1$, wherein $T_1$ is the distance between the first planar top face 206 and the first planar bottom face 208. The first planar top face 206 includes a plurality of recesses 210-214, wherein the recesses in the plurality of recesses 210-214 have differing depths. In an example, the first recess 210 may have a first depth that is 1% of the first thickness, the second recess 212 may have a second depth that is 2% of the first thickness, and the third recess 214 may have a third depth that is 4% of the first thickness. Accordingly, depth of the recesses of a step may be a function of the thickness of the step.

The second step 204 comprises a second planar top face 216 and a second planar bottom face. Here, the gauge 200 is shown as being a unitary structure, such that the first planar bottom face 208 is also the planar bottom face for the second step 204. If the steps are modular, however, the second step 204 will have its own second planar bottom face When the first step 202 is coupled to the second step 204, the first planar bottom face (of the first step 202) and the second planar bottom face (of the second step) are coplanar.

The second step 204 has a second thickness $T_2$ that is greater than the first thickness $T_1$. For instance, $T_2$ can be ½ inch larger than $T_1$. In another example, $T_2$ can be 1 inch larger than $T_1$. The second planar top face 216 comprises a plurality of recesses 218-222. The recesses 218-222 in the second plurality of recesses 218-222 have differing depths. For example, the second plurality of recesses 218-222 includes the fourth recess 218, the fifth recess 220, and the sixth recess 222. The fourth recess 218 may have a fourth depth that is 1% of $T_2$, the fifth recess 220 can have a fifth depth that is 2% of $T_2$, and the sixth recess 222 can have a sixth depth that is 4% of $T_2$.

The first top planar face 206 is of a first length $L_1$ and a first width $W_1$. The second top planar face 216 may have a second length $L_2$ and a second width $W_2$. In an exemplary embodiment, $L_1$ can equal $L_2$ and $W_1$ can equal $W_2$. The first plurality of recesses 210-214 are etched orthogonally to the first length of the top planar surface 206 and extend across the entirety of the first width of the first top planar face 206. Similarly, the second plurality of recesses 218-222 can be etched orthogonally to the second length of the second top planar face 216 and can extend across an entirety of the second width of the second top planar face 216. In an alternative embodiment, the recesses 210-214 and 218-222 need not extend across the entirety of the widths of the first planar top face 206 and the second planar top face 216, respectively. For example, the recesses 210-214 and 218-222 can be etched as squares that are centrally located along the widths of the top planar faces 206 and 216 with lengths of sides being less than the widths of the top planar faces 206 and 216. In another exemplary embodiment, the recesses 210-214 and 218-222 can be etched as circles that are centrally located along the widths of the top planar faces 206 and 216, with diameters being less than the widths of the top planar faces 206 and 216. It is therefore to be understood that the recesses can be any suitable shape.

In the exemplary contrast sensitivity gauge 200, the first plurality of recesses 210-214 are aligned with the second plurality of recesses 218-222. That is, a first edge of the first recess will be in alignment with a corresponding first edge of the fourth recess 218. In an alternative embodiment, recesses in the first plurality of recesses 210-214 can be juxtaposed with recesses in the second plurality of recesses 218-222. It is to be understood that any suitable alignment of recesses across steps in the contrast sensitivity gauge 200 is contemplated.

Figure 3:
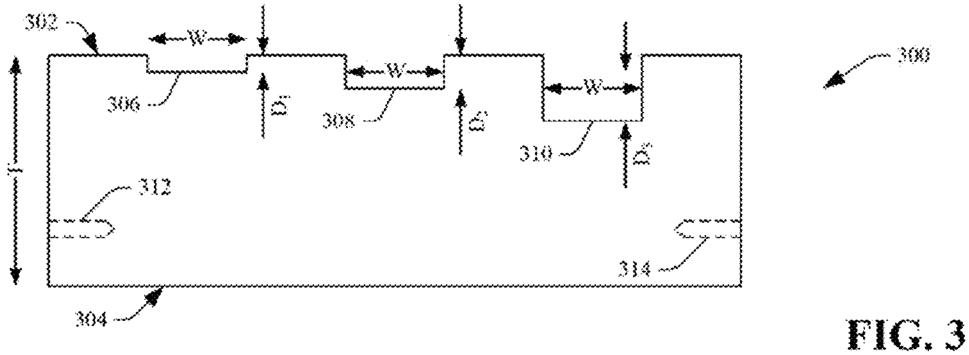
FIG. 3 is a front view of a step in a multi-step contrast sensitivity gauge.

With reference now to FIG. 3, a front view of an exemplary step 300 of a contrast sensitivity gauge is illustrated. The step 300 comprises a top planar face 302 and a bottom planar face 304 with a thickness (T) that is the distance between the top planar face 302 and the bottom planar face 304. Pursuant to a particular example, the thickness of the step 300 can be ½ inch, 1 inch, 1½ inches, 2 inches, 2½ inches, 3 inches, 3½ inches, 4 inches, 4½ inches, 5 inches, 5½ inches, or 6 inches. The top planar face 302 has a plurality of recesses 306-310 therein, wherein depths of the recesses 306-310 are different. In an example, the first recess 306 can have a depth $D_1$ that is 1% of T, the second recess 308 can have a depth $D_2$ that is 2% of T, and the third recess 310 may have a depth $D_3$ that is 4% of T. It is to be understood that a step in contrast sensitivity gauge described herein may include more or fewer recesses than the three shown and described herein, and the depths can be different than 1%, 2%, and 4% of the thickness of the step. These values are provided herein solely for exemplary purposes.

As mentioned above, the recesses 306-310 can extend across a width of the step 300. Pursuant to an example, the widths of each of the recesses 306-310 can be ½ inch. Similarly, a distance between adjacent recesses in the step 300 can be ½ inch. In another example, a distance between an edge of the step and an outermost recess can be 1 inch. Thus, the distance between the recess 306 and the edge of the step can be 1 inch.

The step 300 can also comprise a pair of threaded apertures 312 and 314 that are configured to receive threaded fasteners. The apertures 312 and 314 may be of any suitable diameter. The threaded apertures 312 and 314 are configured to receive threaded fasteners that are employed in connection with coupling different steps to generate a multi-step contrast sensitivity gauge.

Figure 4:
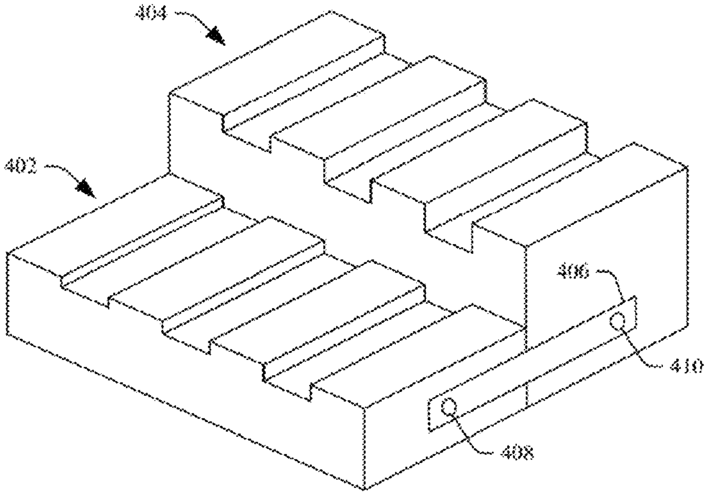
FIG. 4 is a perspective view of a modular multi-step contrast sensitivity gauge.

Now referring to FIG. 4, an exemplary contrast sensitivity gauge 400 that is composed of multiple modular steps is illustrated. Specifically, the gauge 400 comprises a first step 402 and a second step 404. The first step 402 and the second step 404 each include a threaded aperture, such as one of the threaded apertures 312 or 314 shown in FIG. 3. A bracket 406 comprises a plurality of apertures 408 and 410 that correspond to the apertures of the first step 402 and the second step 404. A threaded fastener can be threaded into the threaded aperture of the first step 402, such that the head of the threaded fastener secures the bracket 406 in place. Similarly, a second threaded fastener can pass through the aperture 410 of the bracket 406 and be threaded into the threaded aperture of the second step 404, such that a head of the second threaded fastener holds the bracket 406 in place. This effectively couples the first step 402 with the second step 404 to generate a multi-step contrast sensitivity gauge. While threaded apertures, a bracket, and threaded fasteners have been described as being employed to join the modular steps 402 and 404, it is to be understood that other mechanisms for joining modular steps are contemplated. For instance, the modular steps 402 and 404 can have notches and extensions thereon that allow for the steps to be coupled. Further, a clip can be employed to couple modular steps.

Figure 5:
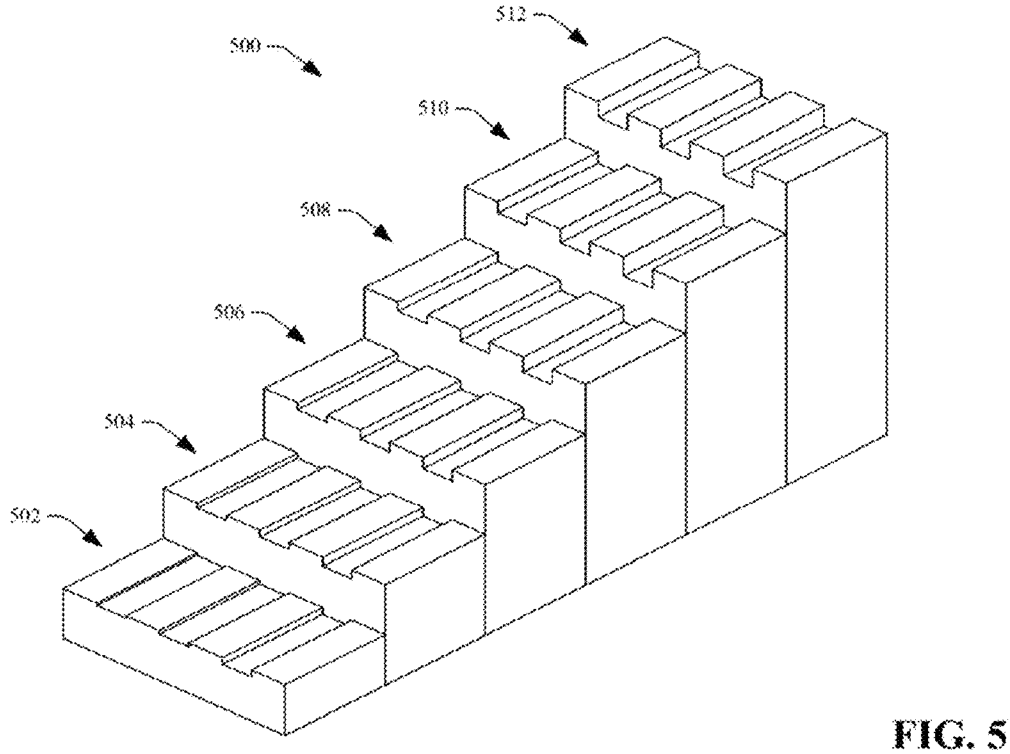
FIG. 5 is a perspective view of an exemplary multi-step contrast sensitivity gauge that comprises six steps.

Turning now to FIG. 5, an exemplary multi-step contrast sensitivity gauge 500 is illustrated. The exemplary gauge 500 includes six different steps 502-512. Each of the steps 502-512 comprises a plurality of recesses that are a function of the respective thicknesses of the steps 502-512. In an example, the sixth step 512 can be at least 6 inches in thickness. In another example, the fifth step 510 can be at least 5 inches in thickness. The gauge 500 can be modular in nature, such that steps can be added or removed from the gauge 500. The gauge 500 can be positioned relative to an X-ray source such that photons emitted from the source first meet the faces of the steps 502-512 with recesses thereon. A resultant X-ray image can be analyzed to indicate a contrast-to-noise ratio for the varying thicknesses of the steps 502-512 and the varying depths of the recesses therein.

Each of the steps may be composed of the same material, wherein such material is the same material that is desirably subject to X-ray imaging in an industrial environment. In an alternative embodiment, the gauge 500 may be composed of steps of differing materials, thereby allowing a reviewer of a resultant X-ray image to characterize quantitatively contrast-to-noise ratio for the detector for differing materials of differing thicknesses with recesses of different depths.

Figure 6:
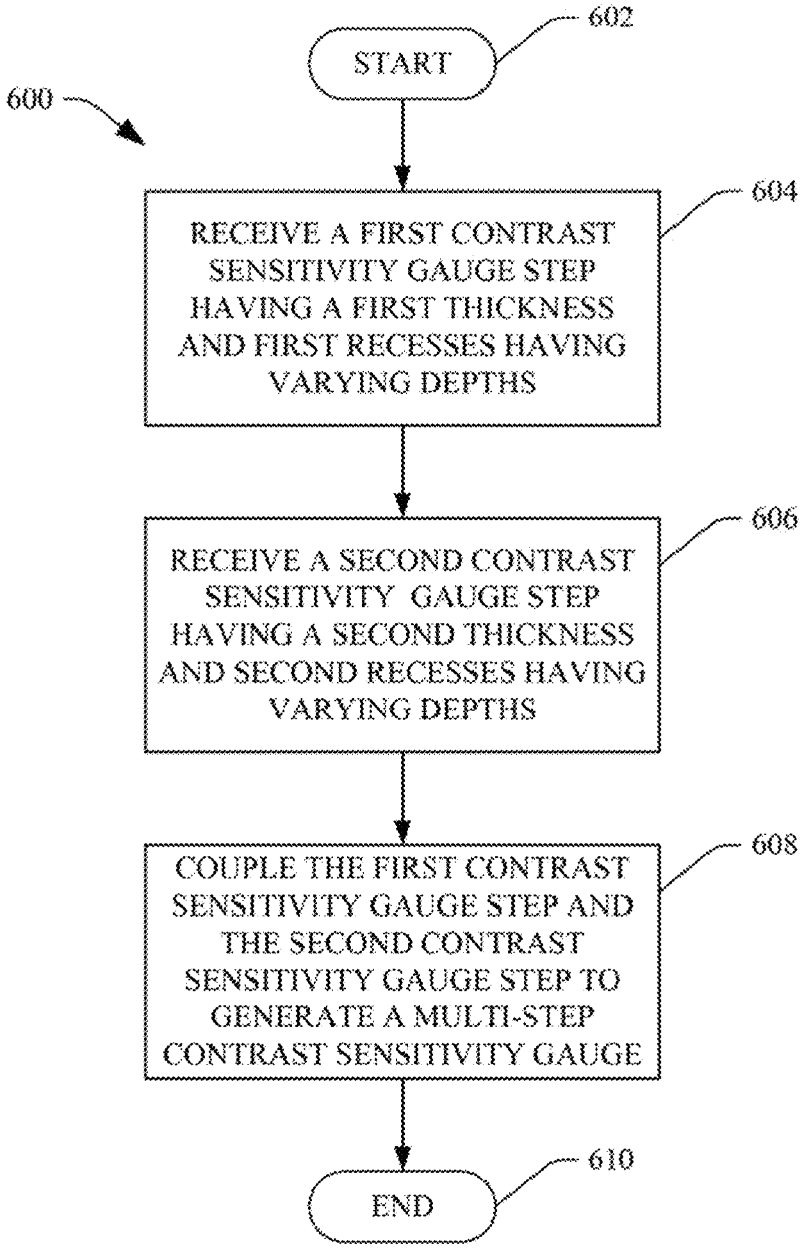
FIG. 6 is a flow diagram that illustrates an exemplary methodology for creating a multi-step contrast sensitivity gauge from a plurality of modular steps.
Figure 7:
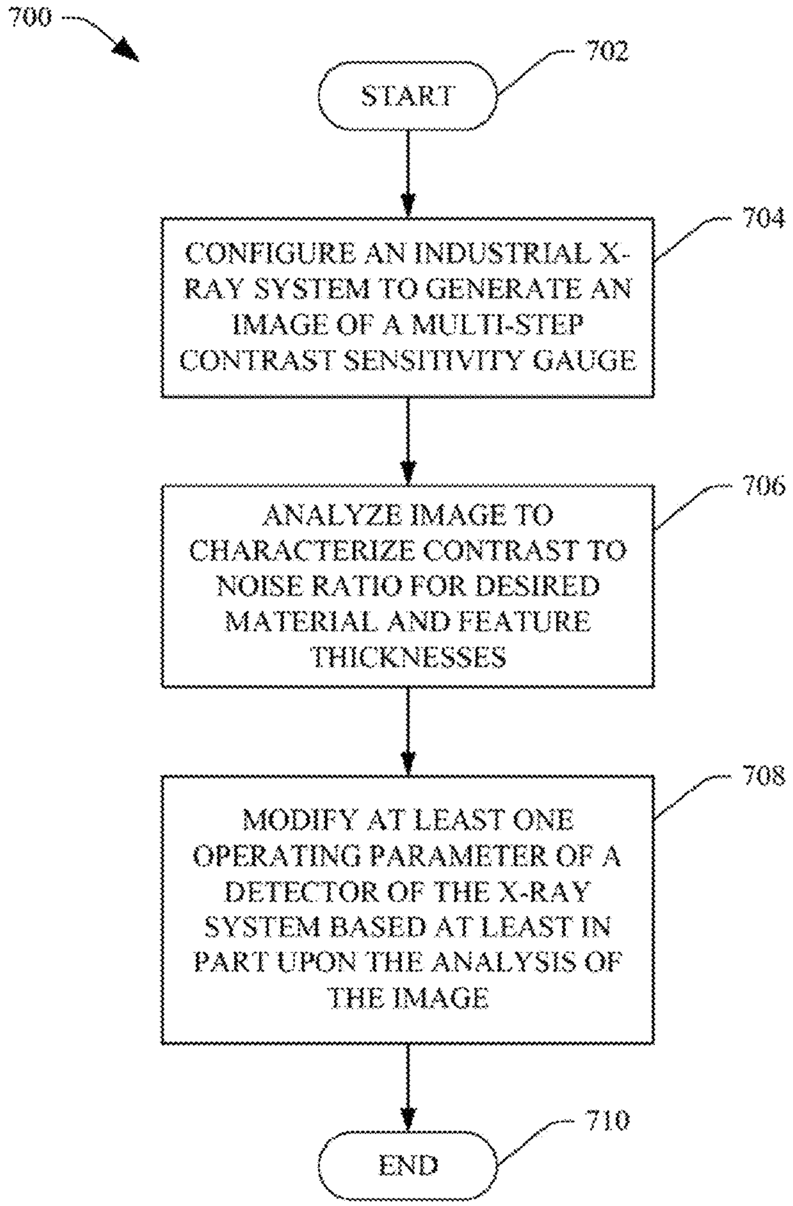
FIG. 7 is a flow diagram that illustrates an exemplary methodology for modifying at least one operating parameter of an X-ray system based at least in part upon a contrast-to-noise ratio computed for a certain material at varying thicknesses.

With reference now to FIGS. 6-7, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Now turning to FIG. 6, an exemplary methodology 600 for composing a multi-step contrast sensitivity gauge out of multiple modular steps is illustrated. The methodology 600 starts at 602, and at 604 a first contrast sensitivity gauge step that has a first thickness and first recesses having varying depths therein is received. Examples of such steps have been presented above.

At 606, a second contrast sensitivity gauge step having a second thickness and second recesses therein having varying depths is received. For example, the second thickness may be greater than the first thickness.

At 608, the first contrast sensitivity gauge step and the second contrast sensitivity gauge step can be coupled to generate a multi-step contrast sensitivity gauge. The methodology 600 completes at 610.

Turning now to FIG. 7, an exemplary methodology 700 for modifying at least one parameter of an X-ray system is illustrated. The methodology 700 starts at 702, and at 704 an industrial X-ray system is configured to generate an image of a multi-step contrast sensitivity gauge. For instance, such gauge may be positioned relative to an X-ray source and a detector such that the X-ray beams emitted from the X-ray source are first incident upon a side of the contrast sensitivity gauge that has recesses therein. The contrast sensitivity gauge can be placed at a known position relative to the X-ray source and/or the detector.

At 706, an image is analyzed to characterize the contrast-to-noise ratio with respect to a desired material thickness and feature thickness. This can be accomplished by analyzing the portions of the image corresponding to a step of a certain thickness and a recess of a certain depth.

At 708, at least one operating parameter of a detector of the X-ray system (or other module in the X-ray system) is modified based at least in part upon the analysis of the image. The methodology 700 completes at 710.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A multi-step X-ray contrast sensitivity gauge, comprising:

a first step comprising:

a first planar top face; and a first planar bottom face, the first planar top face being parallel to the first planar bottom face, the first step having a first thickness between the first planar top face and the first planar bottom face, the first planar top face comprising a first plurality of recesses of differing depths; and a second step comprising:

a second planar top face; and a second planar bottom face, the second planar top face being parallel to the second planar bottom face, the second step having a second thickness between the second planar top face and the second planar bottom face that is greater than the first thickness, the second planar top face comprising a second plurality of recesses of differing depths; the first planar bottom face of the first step being coplanar with the second planar bottom face of the second step.

2. The sensitivity gauge of claim 1, the first planar top face comprising a first recess, a second recess, and a third recess, the first recess having a first depth that is 1% of the first thickness, the second recess having a second depth that is 2% of the first thickness, and the third recess having a third depth that is 4% of the first thickness, the second planar top face comprising a fourth recess, a fifth recess, and a sixth recess, the fourth recess having a fourth depth that is 1% of the second thickness, the fifth recess having a fifth depth that is 2% of the second thickness, and the sixth recess having a sixth depth that is 4% of the second thickness.

3. The sensitivity gauge of claim 1 being a unitary structure.

4. The sensitivity gauge of claim 1, the first step and the second step being modular steps.

5. The sensitivity gauge of claim 4, the first step comprising a first threaded aperture and the second step comprising a second threaded aperture, the first and second apertures configured to receive a first threaded fastener and a second threaded fastener, respectively, the sensitivity gauge of claim 4 further comprising:

a bracket that is operative to couple the first step and the second step, the bracket comprises a first bracket aperture and a second bracket aperture that receive the first threaded fastener and the second threaded fastener, respectively.

6. The sensitivity gauge of claim 1, wherein a difference between the first thickness and the second thickness is approximately one inch.

7. The sensitivity gauge of claim 1, the first planar top face having a first length and a first width, the first plurality of recesses each extending the first width of the first planar top face.

8. The sensitivity gauge of claim 7, wherein the recesses in the first plurality of recesses have identical widths of approximately 0.5 inches.

9. The sensitivity gauge of claim 7, the second planar top face having a second length and a second width, the second plurality of recesses each extending the second width of the second planar top face, the recesses in the first plurality of recesses being in alignment with the recesses in the second plurality of recesses.

10. The sensitivity gauge of claim 1 being composed of one of stainless steel, iron, aluminum, brass, Lucite, or Poly (methyl methacrylate).

11. The sensitivity gauge of claim 1, wherein the second thickness is at least six inches.

12. The sensitivity gauge of claim 1, further comprising a plurality of other steps each having respective planar top surfaces that comprise recesses of varying depths.

13. A system, comprising:

an X-ray contrast sensitivity gauge that comprises a plurality of steps of varying thicknesses, each step in the plurality of steps comprising a top face and a plurality of recesses, wherein depths of the plurality of recesses are a function of a thickness of the step associated therewith;

an X-ray source that is positioned to project X-rays onto top faces of the steps in the X-ray contrast sensitivity gauge; and a detector that detects an amount of attenuation of the X-rays caused at least partially by the X-ray contrast sensitivity gauge.

14. The system of claim 13, wherein a thickness of a step in the plurality of steps is at least five inches.

15. The system of claim 13, wherein depths of the recesses on a step in the X-ray contrast sensitivity gauge are approximately 1% of a thickness of the step, approximately 2% of the thickness of the step, and approximately 4% of the thickness of the step.

16. The system of claim 13, further comprising a computing device that generates an image based at least in part upon the amount of attenuation detected by the detector, the image indicative of a contrast-to-noise ratio of the detector for a step thickness and recess depth.

17. The system of claim 13, the steps of the X-ray contrast sensitivity gauge being modular.

18. The system of claim 13, the X-ray source emitting X-rays at an energy above 5 MeV.

19. The system of claim 13, the X-ray source emitting X-rays at an energy above 20 MeV.

20. An X-ray contrast sensitivity gauge, comprising:

a plurality of modular steps of differing thicknesses, each modular step in the plurality of modular steps comprising a plurality of recesses with differing depths that are a function of a thickness of the step associated therewith; and coupling means that couples the plurality of modular steps.

* * * * *